United States Patent [19]

Yamada et al.

[11] 3,998,885
[45] Dec. 21, 1976

[54] METHOD OF SEPARATING COMPONENTS OF NITROOXIDATION REACTION MIXTURE

[75] Inventors: Shizuo Yamada; Hiroo Sasaki; Tetsuo Tanaka, all of Shin-nanyo, Japan

[73] Assignee: Toyo Soda Manufacturing Co., Ltd., Japan

[22] Filed: June 18, 1973

[21] Appl. No.: 371,309

[30] Foreign Application Priority Data

June 16, 1972  Japan ............................ 47-60246

[52] U.S. Cl. ...................... 260/586 P; 260/586 R; 423/396
[51] Int. Cl.$^2$ ................. C07C 76/02; C07C 76/06; C07C 45/02; C07C 45/24
[58] Field of Search ....... 260/586 R, 586 A, 586 P, 260/586 M

[56] References Cited

UNITED STATES PATENTS

| 3,637,839 | 1/1972 | Tanaka et al. ................. 260/586 R |
| 3,657,349 | 4/1972 | Lachowicz et al. ............ 260/586 R |
| 3,806,547 | 4/1974 | Pivawer ......................... 260/586 R |
| 3,895,071 | 7/1975 | Kablaoui et al. .............. 260/586 R |

*Primary Examiner*—Norman Morgenstern
*Attorney, Agent, or Firm*—Oblon, Fisher, Spivak, McClelland & Maier

[57] ABSTRACT

2-Nitrocycloalkanone, 2-nitrocycloalkenone or 2-nitrocycloalkadienone is separated from the nitrooxidation reaction mixture of a cyloalkene, a cycloalkadiene or a cycloalkatriene with oxygen and nitrogen oxide by contact with gaseous ammonia.

10 Claims, No Drawings

METHOD OF SEPARATING COMPONENTS OF NITROOXIDATION REACTION MIXTURE

BACKGROUND OF THE INVENTION

1. Field of the Invention

This invention relates to a method for separating α-nitrocycloalkanone, α-nitrocycloalkenone or α-nitrocycloalkadienone from a reaction mixture prepared by the nitrooxidation of a cycloalkene, a cycloalkadiene, or a cycloalkatriene. More particularly, this invention relates to the separation of α-nitrocycloalkanone (NCA) from a reaction mixture in which a cycloalkene, a cycloalkadiene or a cycloalkatriene is reacted with oxygen and a nitrogen dioxide (hereinafter designated generically as $NO_2$) by contacting the mixture with a catalyst of a polar compound, and then treating the reaction solution with ammonia.

2. Description of the Prior Art

α-Nitrocycloalkanone, α-nitrocycloalkenone and α-nitrocycloalkadienone (NCA) are raw materials for the preparation of such useful materials as nylon. However, NCA has not heretofore been produced by an economically satisfactory method. Even under optimum process conditions, it has been necessary to use expensive reactants, such as cycloalkanone and acetic anhydride for the production of NCA.

NCA has been prepared by the present inventors by the reaction of cycloalkene, nitrogen dioxide, oxygen and a catalyst of DMSO, DMF, DEF, MPP, DMA, etc. which technique has proven to be substantially simpler and more economical than prior art conventional techniques. At a reaction temperature of $-50°$ C to approximately $+20°$ C, α-nitrocycloalkylperoxynitrate is produced. The α-nitrocycloalkylperoxynitrate is denitrated by addition of the reaction mixture to a catalyst containing solution of DMF, whereby NCA is produced.

NCA has also been produced by the one step reaction of admixing nitrogen dioxide and oxygen with a mixture of cycloalkene and a catalyst at $-50°$ C $- +50°$ C whereby an α-nitrocycloalkylperoxynitrate is formed and denitrated. The reaction mixture contains a solvent, a catalyst, NCA, nitric acid, cycloalkene and nitrated by-products such as 2-nitrocycloalkanol and 2-nitrocycloalkylnitrate and a small amount of other unknown materials and the like.

In the past it has been difficult and troublesome to effectively separate NCA and the catalyst by simple evaporation and distillation techniques in high yield because of the presence of the strong oxidizing agent, i.e. nitric acid, because a complex of nitric acid and the catalyst is formed and because nitric acid and the catalyst are not easily vaporized. In addition, NCA and the catalyst are thermally and chemically unstable. In the past, one method of purification of NCA has been to first extract the by-product nitric acid with water from the reaction mixture so that NCA might easily be separated, and then purify NCA by recrystallization followed by separation. However, recrystallization is not an effective method of purification because the reaction mixture contains other nitrated by-products which have structures similar to NCA. Since the difference in solubility of these by-products in the solvents is small, the recrystallization efficiency is negligible. Moreover, the reaction mixture contains unreacted cycloalkene, while cycloalkane impurities and the like are present in the cycloalkene raw material (for example, 5 – 10% of cyclododecane is present in the cyclododecene raw material). The unreacted cycloalkene and the cycloalkane impurities are relatively soluble in non-polar solvents, while the nitrated by-products are soluble in polar solvents. Thus, in order to remove these two types of impurities, which have different solubilities in different solvents, by recrystallization, it is necessary to use repetative recrystallizations in different solvents to purify the product. However, NCA is relatively soluble in both polar solvents and non-polar solvents, which results in relatively high losses of NCA upon recrystallization. Heretofore, no more than 90% of the NCA has been recovered when NCA is purified by recrystallization. Moreover, the main by-products of the nitrooxidation, 2-nitrocycloalkanol and 2-nitrocycloalkyl nitrate, can be converted to NCA, which makes it highly desirable to recover them in high purity. It is also difficult to recover the by-products by recrystallization. For example, 2-nitrocycloalkanol can be converted to NCA by dehydrogenating the alkanol with an oxidizing agent, while 2-nitrocycloalkylnitrate can be converted to NCA by hydrolyzing the nitrate to yield 2-nitrocycloalkanol and then dehydrogenating the alkanol. Thus, the two by-products as a mixture can be treated to form NCA. However, when the by-products are converted to NCA, NCA should not be present in the reaction mixture because when 2-nitrocycloalkylnitrate is hydrolyzed by mineral acid at high temperatures, NCA undergoes sidereactions.

A need, therefore, exists for a method by which NCA can be obtained in high purity and high yield from reaction solutions. It has been found that since NCA reacts differently with ammonia than other nitrated by-products, NCA can be selectively precipitated as the ammonium salt by treatment with ammonia gas in an organic solvent.

SUMMARY OF THE INVENTION

Accordingly, one object of this invention is to provide a method of separating α-nitrocycloalkanone from the nitrooxidation reaction mixture of a cycloalkene, cycloalkadiene or cycloalkatriene.

Briefly this object and other objects of this invention as hereinafter will become more readily apparent have been attained by contacting ammonia gas with the nitrooxidation reaction mixture of a cycloalkene, cycyloalkadiene or a cycloalkatriene.

DESCRIPTION OF THE PREFERRED EMBODIMENTS

The ammonium salt of α-nitrocycloalkanone (NCA) is a pale yellowish green powder which is sparingly soluble in organic solvents except those solvents which have active hydrogen atoms such as the lower alcohols. (NCA or α-nitrocycloalkanone is used herein in the generic sense for α-nitrocycloalkanone, α-nitrocycloalkenone and α-nitrocycloalkadienone.) This solubility property of the ammonium salt of NCA, i.e. its sparing solubility in certain organic solvents, is very important. Use is made of this fact to remove impurities (nitrated by-products and unreacted cycloalkene) from NCA by washing NCA with a solvent.

It has been found that the ammonium salt of α-nitrocyclododecanone as an example of an ammonium salt of NCA can be easily decomposed by heating the salt to form stoichiometric quantities of NCA and ammonia. As an example, when α-nitrocyclododecanone is produced, the ammonium salt of α-nitrocyclododecanone is separated and heated in a solvent to yield α-nitrocyclododecanone. It is difficult to obtain α-nitrocyclooctanone or α-nitrocyclohexanone in high yields by heating the corresponding ammonium salt because ω - or ε -nitroalkanoamides are easily produced as by-products. However, the ammonium salts of NCA compounds can be directly used for the preparation of ω-nitroalkanoic acids, or more specifically ε-nitrocaproic acid, or a derivative thereof. The latter is useful for the production of such materials as nylon.

It has been found that when a reaction solution containing NCA is subjected to ammonia, not only is the separation of NCA accomplished, but the catalyst can also be separated and recovered in high yield and with high efficiency. The method of recovering the catalyst is very effective when a nonaqueous reaction system is involved in the production of NCA. Prior separation techniques for NCA have involved the removal of nitric acid and the catalyst from the reaction mixture with water. The catalyst is subsequently recovered by neutralizing the nitric acid with an aqueous solution of an alkali salt. However, if water is used to recover the catalyst, several disadvantages accrue as follows.

In the recovery of the catalyst, it is necesary to evaporate water. The nitrate anion is a strong oxidizing agent. When the solution containing the nitrate anion and the organic catalyst is heated to evaporate the water, loss of the catalyst results, and occasionally explosions can occur. If water is used to aid in catalyst removal, water will be present in the nitrooxidation solvent system which is disadvantageous. Thus, it is necessary to remove water from the solvent, when the solvent is recycled. If water is present in the nitrooxidation system, nitric acid is formed by the reaction of nitrogen dioxide with water resulting in the loss of nitrogen dioxide, and the water will react with the intermediate, 2-nitrocycloalkylperoxynitrate to yield such by-products as 2-nitrocycloalkanol, or the like.

It is preferable therefore, not to use water in the reaction system. However, if the catalyst is separated from the reaction solution without the use of water, other difficulties may nevertheless arise. At least a portion of the catalyst forms a complex with the nitric acid by-product which makes it difficult to recover the catalyst. Thus, when the nitric acid is neutralized with an alkali to form an alkali nitrate salt, the catalyst is either freed from its nitrate complex or the catalyst forms a different complex with the alkali nitrate salt produced which is easier to treat than the complex of the catalyst and nitric acid. However, if the complex of the catalyst and nitric acid is neutralized in an organic solvent, the amount of catalyst lost is substantially greater than when the neutralization is accomplished in an aqueous solution. In aqueous solutions, the bond between the catalyst and the nitric acid is weakened by solvation with water, which minimizes catalyst loss even though strong alkalis such as sodium hydroxide are used to neutralize the nitric acid. On the other hand, coordination of solvent molecules to the complex is weak especially in solvents suitable for the nitrooxidation reaction. Thus, the bond between the catalyst and the nitric acid is too strong, which results in rapid deterioration of the catalyst when the nitric acid is neutralized. Moreover, solid alkalis are usually insoluble in organic solvents of the type used in nitrooxidation reactions, so that when a solid alkali is used, it is difficult to neutralize nitric acid.

When nitric acid is neutralized by directly adding an alkali to the reaction mixture, the resulting NCA and the nitro by-products are very reactive with alkali. This reaction can be severe when the neutralization of the nitric acid with alkali is not smooth. If NCA and the other nitro by-products are neutralized before neutralization of the nitric acid, the alkali salts of the nitro compounds are neutralized by nitric acid in the reaction system. When this happens, the Nef reaction occurs with the nitro compound to yield undesirable carbonyl compounds. Under these conditions the desired nitro compound is not recovered and various by-products are formed.

As stated before, preferably the catalyst is separated and recovered without using water, even though in the past when water was not used the neutralization of the nitric-acid complex was very difficult. As a result of a series of investigations concerning this problem, it has been found that the problem can be solved by neutralization of the nitric acid with ammonia gas. When ammonia gas is used as the alkali, the neutralization of the acid solution can be smoothly conducted because ammonia is a gas and permeates rapidly to all parts of the reaction solution. Consequently, no substantial loss of catalyst occurs during the neutralization of the nitric acid in the organic solvent. Under these conditions when the ammonium salt of NCA is neutralized with nitric acid in the organic solvent, NCA can be stoichiometrically recovered without any apparent loss due to Nef's reaction as the ammonium salt of the aci-isomer of NCA. Ammonia gas is used for the neutralization of nitric acid in the presence of NCA, even though NCA is neutralized before the neutralization of nitric acid and the ammonium salt of NCA is neutralized with nitric acid. No apparent loss of NCA has been found when this tecnhique is used. This is especially important when substantial amounts of the catalyst — nitric acid complex precipitates in the nitrooxidation reaction, because, if alkali is directly added to the reaction mixture, neutralization of NCA will occur before neutralization of the nitric acid, consequently neutralization of the ammonium salt of NCA with nitric acid will occur. When ammonia is used to neutralize the reaction solution, undesirable side-reactions involving the product nitro compounds do not occur. This is true even when large excessive amounts of ammonia are used in relation to nitric acid.

A small amount of an unknown material is present in the nitrooxidation reaction solution as a by-product which has a high reactivity with ammonia and forms a colored material (reddish-brown). This material is sparingly soluble in most organic solvents except alcohols. Thus, it can be easily separated from NCA and other nitro compounds simply by recrystalization. This is another advantage to the use of ammonia, because the unknown by-product reacts with ammonia and is converted to the colored material which is easily separated from NCA and other by-products.

It is clear from the description, therefore, that NCA and/or the catalyst can be separated from the nitrooxidation reaction mixture of a cycloalkene by the process of this invention, by subjecting the reaction mixture or the reaction mixture from which the catalyst and nitric acid have been removed to ammonia gas.

The nitrooxidation reaction mixture is usually a uniform solution. However, if the catalyst — nitric acid complex precipitates from solution, the reaction solution will become nonuniform. In some cases, even though the reaction mixture is liquid it may separate into a lower layer containing the catalyst (including most of the nitro compounds and nitric acid) and an upper layer consisting mainly of solvent (including unreacted cycloalkene). For example, when DMF, DEF, MPD, DMA, or the like is used as the catalyst, the catalyst - nitric acid complex does not precipitate from the solution except when an aliphatic hydrocarbon solvent is used and the reaction mixture remains uniform. On the other hand, in many instances when DMSO is used as the catalyst, at least a part of the catalyst - nitric acid complex precipitates from solution to form a nonuniform system. As an example, when DMSO is used as the catalyst and carbon tetrachloride, ether or trichloroethane is used as the solvent, precipitation of the complex is promoted. On the other hand, when benzene, toluene, or the like is used as the solvent, only a portion of the complex precipitates. However, when methylene chloride is used as the solvent, even though DMSO is used as the catalyst, no complex precipitates. When an aliphatic hydrocarbon such as n-hexane is used as the solvent, the nitrooxidation reaction mixture containing one of the catalysts of the invention separates into a catalyst layer and a solvent layer. The nitro product compounds and nitric acid are found mainly in the catalyst layer, while the unreacted cycloalkene is found mainly in the solvent layer.

The reaction conditions for the nitrooxidation reaction mixture differ depending upon the selection of the catalyst and the solvent. In any case, ammonia can be supplied directly or after dilution to the reaction mixture. If necessary, ammonia can be supplied after the nitric acid and catalyst are removed. Although catalyst recovery is somewhat affected, it is possible to separate NCA by treatment with ammonia after the catalyst and nitric acid have been removed from the reaction mixture with water.

When ammonia is directly supplied to the nitrooxidation reaction mixture, nitric acid is initially neutralized. At the same time the neutralization of nitric acid is completed, small amounts of the unknown material which has a high reactivity with ammonia, react to form a tacky solid which has a reddish brown color. The neutralization of NCA then occurs. It is possible to continue the supply of ammonia to the solution to neutralize NCA and to separate ammonium nitrate, by-products and the ammonium salt of NCA as a mixture, and subsequently to purify NCA and ammonium nitrate. However, usually, the neutralization is discontinued at each stage to separate the impurities so that the ammonium salt of NCA and ammonium nitrate are obtained in high purity. That is, the neutralization is discontinued after the nitric acid is neutralized and the resulting ammonium nitrate is separated. When the by-products are precipitated by the neutralization with ammonia, neutralization is also discontinued and the by-products are removed. The neutralization of the solution is then continued to yield the highly pure ammonium salt of NCA. The manner in which the catalyst functions depends upon the type of the catalyst and solvent. If DMF, DEF or MPD is used as the catalyst, the catalyst is completely dissolved in the solvent after neutralizing the nitric acid with ammonia. In these cases, the catalyst remains in the filtrate after the ammonium salt of NCA is filtered. On the other hand, if DMSO is used as the catalyst, a DMSO solution containing ammonium nitrate usually separates from the reaction mixture as a second layer. In the former case, the catalyst is present in a free state in the filtrate and the solvent is first recovered and then the catalyst can be recovered by evaporation or by distillation. In the latter case, most of the catalyst can be recovered together with ammonium nitrate simply be separating the two phases after the neutralization of nitric acid.

However, when DMSO is used as the catalyst, a special solvent such as methylene chloride is used as the solvent. As a result, ammonium nitrate precipitates from solution and DMSO mixes with the solvent because of the special affinity between DMSO and the solvent. The procedures described show methods by which ammonia is directly supplied to the nitrooxidation reaction mixture. However, when DMSO is used as the catalyst and a DMSO - nitric acid complex precipitates at a high rate, the precipitated complex can first be filtered and then the nitric acid and NCA can be neutralized separately. In this case, the complex can be neutralized alone, or it can be first dissolved or suspended in a fresh solvent and then neutralized. Especially when methylene chloride is used as the solvent, the solid ammonium nitrate precipitate can be easily separated. In this case, a portion of the catalyst is recovered as a methylene chloride solution, and the remainder is recovered from the filtrate after the neutralization and separation of NCA.

When an aliphatic hydrocarbon such as n-hexane is used as the solvent, and the nitrooxidation reaction mixture separates into two layers, the upper layer can be neutralized after separation of the lower catalyst layer. In this case, ammonium nitrate and the ammonium salt of NCA are fairly well dissolved in the polar solvent, so that it is difficult to completely precipitate ammonium nitrate and the ammonium salt of NCA, by simply subjecting the products to ammonia gas. Thus, the reaction mixture should be diluted with a suitable solvent such as an aromatic hydrocarbon and then ammonia gas is supplied in the same manner as in the treatment of the nitrooxidation reaction mixture using the solvent.

The neutralization and the separation of NCA is preferably conducted in the temperature range of −30° C to 60° C. The lower temperature limit is not critical. However, certain economic advantages can not be achieved at the lower temperatures. The optimum temperature for the neutralization depends upon the type of solvent. For example, when n-hexane is used as the solvent, a sufficient amount of the ammonium salt of NCA is precipitated by supplying ammonia at temperatures up to 50° C. However, when toluene is used as the solvent, the ammonium salt of NCA does not precipitate when ammonia is supplied at temperatures at about 30° C. That is, when an aliphatic hydrocarbon is used as the solvent, the optimum temperature range is −10° to 40° C. When an aromatic hydrocarbon or a halo-hydrocarbon or ether is used as the solvent, the optimum temperature range is −10° − 20° C.

The neutralization reaction is preferably conducted under slight pressures of ammonia. However, atmospheric pressures can be used. When the amount of ammonia used is about a 2 − 3 mole ratio to NCA, more than 98% of the NCA can be precipitated as the ammonium salt of NCA. The neutralization of nitric acid in the nitrooxidation reaction mixture can be performed at temperatures between −50° − +80° C. In order to minimize loss of the catalyst and NCA, it is preferable to conduct the neutralization at temperatures of −10° − +30° C. When nitric acid is neutralized in the stated temperature range, it is possible to neutralize NCA after neutralizing nitric acid at the same temperature.

As should be clear from this discussion, this invention makes it possible to separate NCA as the ammonium salt of NCA from the nitrooxidation reaction mixture of a cycloalkene in high efficiency. Usually, it is possible to separate more than 98% of the NCA from the reaction mixture without any contamination by nitro by-product compounds in a one step operation. It is difficult to attain these results by conventional recrystallization methods.

By the method of this invention, it is possible to recover the catalyst from the nitrooxidation reaction mixture in high yields. Thus, the objects of the invention can be attained without the use of water. Moreover, the by-products such as 2-nitrocycloalkanol and 2-nitrocycloalkyl nitrate can be recovered as concentrated materials essentially free of NCA. Moreover, the nitric acid by-product can be recovered as ammonium nitrate which is useful in industrial processes.

Having generally described this invention, a further understanding can be obtained by reference to certain specific examples which are provided herein for purpose of illustration only and are not intended to be limiting unless otherwise specified.

The nitrooxidation reaction as conducted by the general procedure indicated below except for Examples 7 and 9. The nitrooxidation reaction of Examples 7 and 9 is shown in the examples.

NITROOXIDATION REACTION

A 0.30 mole quantity of cycloalkene and 0.45 mole of the catalyst were dissolved in 600 cc of a solvent, and the mixture was stirred at 0° C. A mixture of $NO_2$ and $O_2$ in a molar ratio of 1 : 5 was introduced into the mixture, (0.50 mole of $NO_2$ was charged during a 4 hour period) and the mixture was stirred for 30 minutes to complete the reaction. At the end of the reaction, a portion of the reaction mixture was sampled and the unreacted cycloalkene was measured by gas chromatography in order to measure the conversion of the cycloalkene. The product 2-nitrocycloalkanone (NCA) was measured by its infrared spectrum. The yield of NCA in the nitrooxidation reaction in the following examples will be shown in mole % based on the amount of cycloalkene consumed in the reaction.

EXAMPLE 1

Nitrooxidation Condition:
 Cycloalkene — cyclododecene
 Catalyst — DMF
 Solvent — toluene The nitrooxidation reaction mixture was a completely uniform solution. Ammonia was injected with stirring into the reaction mixture at 0° C to neutralize the nitric acid. When the neutralization of the nitric acid was finished and the color of the reaction mixture had suddenly changed, the injection of ammonia was stopped and the precipitated ammonium nitrate was filtered. The yield of ammonium nitrate was 17.6 g (0.220 mole) after washing and drying the impure ammonium nitrate obtained. Then ammonia was slowly injected into the filtrate to precipitate the colored by-product material. After 0.04 of ammonia was injected, the injection of ammonia was stopped and the colored material as filtered and removed. Ammonia was injected into the filtrate at the rate of 0.14 g/min to neutralize the 2-nitrocyclododecanone in solution. After 60 minutes, the injection of ammonia was stopped and nitrogen gas was flushed through the flask to remove excess ammonia, and then the precipitated ammonium salt of 2-nitrocyclododecanone was filtered.

The resulting ammonium salt as washed with 50 cc of cooled toluene and 100 cc of cooled n-hexane and the ammonium salt was dried under reduced pressure and was weighed. A 52.8 g quantity (0.216 mole) of the ammonium salt of 2-nitrocyclododecanone as obtained. An infrared spectrum (KBr tablet) of a sample of the product revealed the broad absorption for ammonium salts at about 3100 $cm^{-1}$. The elementary analysis of the product was as follows:

|  | C | H | N |
|---|---|---|---|
| Found | 59.02% | 9.94% | 11.23% |
| Calculated | 58.99% | 9.90% | 11.46% |

Toluene was distillated under reduced pressure from the filtrate which included the wash solution after filtering the ammonium salt, and 32.1 g (0.439 mole) of the DMF catalyst was recovered by distillation. Only 0.45 g (0.002 mole) of 2-nitrocyclododecanone remained in the filtrate. A 1.1 g amount (0.005 mole) of 2-nitrocyclododecanol and 1.7 g (0.006 mole) of 2-nitrocyclododecylnitrate remained in high concentration in the residue after distillating toluene, DMF and cyclododecene from the filtrate.

The yield of 2-nitrocyclododecanone from the nitrooxidation reaction was 89.3%, and the amount of 2-nitrocyclododecanone recovered as the ammonium salt was 99.1%. The amount of DMF catalyst recovered was 97.5%.

EXAMPLE 2

Nitrooxidaton Conditions:
 Cycloalkene — cyclododecene
 Catalyst — DMSO
 Solvent — toluene A DMSO - nitric acid precipitate was found in the nitrooxidation reaction mixture. Ammonia was injected into the stirred reaction mixture at 0° C to neutralize the nitric acid produced. No ammonium nitrate precipitate was found in Example 1. After neutralization of the nitric acid and the sudden change in color of the reaction mixture, the injection of ammonia was stopped and the reaction mixture was transferred to a separatory funnel. The DMSO layer containing ammonium nitrate separated as the lower layer and the lower layer was withdrawn. Gas chromatographic analysis revealed that only 1.40 g (0.018 mole) of DMSO was present in the upper toluene layer. The upper layer was transferred to a flask, and ammonia was slowly injected into it to precipitate a colored material. After 0.04 g of ammonia was supplied, the injection of ammonia was stopped and the colored material as filtered. Ammonia was injected into the filtrate at a rate of 0.14 g/min., to neutralize 2-nitrocyclododecanone. After 60 minutes, the injection of ammonia was stopped, and nitrogen gas was flushed through the container to remove excess ammonia, and the resulting ammonium salt of 2-nitrocyclododecanone was filtered.

In accordance with the procedure of Example 1, 53.7 g (0.220 mole) of the ammonium salt of 2-nitrocyclododecanone was obtained. In addition, toluene and 1.19 g (0.015 mole) of DMSO were recovered by distillation of the filtrate obtained by filtering the ammonium salt of 2-nitrocyclododecanone. A 0.21 g amount of 2-nitrocyclododecanone remained in the filtrate. A 0.91 g amount (0.004 mole) of 2-nitrocyclododecanol and 1.7 g (0.006 mole) of 2-nitrocyclododecylnitrate were present in high concentration in the residue after recovering toluene, DMSO and cyclododecene.

The DMSO solution containing ammonium nitrate was separated in a separatory funnel and was admixed with 500 cc of methylene chloride until ammonium nitrate had precipitated and the solution was filtered. DMSO was distilled and recovered from the filtrate after removal of methylene chloride. The amount of DMSO recovered including the DMSO recovered from the filtrate after separating the ammonium salt of 2-nitrocyclododecanone was 96.8%. The yield of 2-nitrocyclododecanone from the nitrooxidation reaction was 91.2%. The amount of 2-nitrocyclododecanone recovered as the ammonium salt in the separation step was 99.5%.

EXAMPLE 3

Nitrooxidation Condition:
  Cycloalkene — cyclododecene
  Catalyst — DMSO
  Solvent — ether An appreciable quantity of a DMSO-nitric acid complex was found in the reaction mixture. The reaction mixture was stirred at 0° C and ammonia was slowly injected to neutralize the nitric acid. When a new precipitate had appeared after the original complex had redissolved, the injection of ammonia was stopped. The DMSO layer containing ammonium nitrate separated as the lower layer, and the lower layer was withdrawn.

Ammonia was slowly injected into the upper phase. After 0.04 g of ammonia was added to the upper phase, the injection of ammonia was stopped and the precipitated colored material was filtered. Ammonia was further injected into the filtrate at a rate of 0.14 g/min. to neutralize 2-nitrocyclododecanone. After 60 minutes, the injection of ammonia was stopped and the reaction mixture was treated in the same manner as in Example 1 to yield 49.6 g (0.203 mole) of the ammonium salt of 2-nitrocyclododecanone.

The solvent, unreacted cyclododecene and 2.4 g (0.031 mole) of DMSO were recovered from the filtrate by distillation. In addition, 500 cc of methylene chloride was added to the DMSO solution containing ammonium nitrate to precipitate ammonium nitrate. The precipitated ammonium nitrate was filtered and 31.5 g (0.403 mole) of DMSO was recovered by distillation from the filtrate.

The yield of 2-nitrocyclododecanone from the nitrooxidation reaction was 83.8%. The amount of 2-nitrocyclododecanone recovered as the ammonium salt was 98.7% in the separation step. The recovery rate of the DMSO catalyst was 96.4%.

EXAMPLE 4

Nitrooxidation Condition:
  Cycloalkene — cyclododecene
  Catalyst — DMSO
  Solvent — carbon tetrachloride Most of the DMSO-nitric acid complex formed in the reaction system was precipitated as solid and filtered. The complex was very hygroscopic and the filtration had to be conducted under a dry atmosphere. Ammonia was injected into the filtrate obtained by filtering the complex at 0° C at a rate of 0.14 g/min for 60 minutes. The resulting solid (ammonium salt of 2-nitrocyclododecanone and a small amount of ammonium nitrate and colored material), was filtered, washed and transfered to a 500 cc flask. A 300 cc volume of toluene was added to the solid and the stirred mixture was heated at 60° C. Nitrogen gas was injected into the stirred solution to remove the ammonia for 20 minutes until most of solid had dissolved. The resulting solution was cooled to room temperature, and then the residual solid (ammonium nitrate, colored material and ω-nitrododecanoic amide) was filtered and toluene was distilled from the filtrate to yield 49.3 g (0.217 mole) of crude 2-nitrocyclododecanone, which contained a small of ω-nitrododecanoic amide. A 300 cc volume of n-hexane was added to the crude product which was heated at 60° C to dissolve the product. ω-Nitrodocecanic amide was removed as the insoluble material. n-Hexane was distillated from the solution to yield 48.9 g (0.215 mole) of the ammonium salt of 2-nitrocyclododecanone. Carbon tetrachloride and 17.0 g (0.218 mole) of DMSO were recovered by distillation from the filtrate which was separated from the ammonium salt of 2-nitrocyclododecanone.

In addition, the DMSO-nitric acid complex separated from the nitrooxidation reaction mixture was dissolved in 300 cc of methylene chloride. Ammonia was injected into the solution at 10° C to neutralize the nitric acid. The precipitated ammonium nitrate was filtered, washed and dried to yield 16.2 g (0.202 mole) of ammonium nitrate. A 16.6 g amount (0.213 mole) of DMSO was recovered by distillation under reduced pressure from the filtrate.

The yield of 2-nitrocyclododecanone from the nitrooxidation reaction was 90.7%. The amount of 2-nitrocyclododecanone recovered as the ammonium salt in the separation step was 97.7%. The amount of DMSO catalyst recovered was 95.8%.

EXAMPLE 5

Nitrooxidation Condition:
  Cycloalkene — cyclododecene
  Catalyst — DMSO
  Solvent — methylene chloride The nitrooxidation reaction mixture was completely uniform. Ammonia was injected into the stirred reaction mixture at 0° C to neutralize the nitric acid. The injection of ammonia was stopped when the color of the solution changed after the neutralization of nitric acid. The precipitated ammonium nitrate was filtered, washed and dried. A 15.9 g (0.199 mole) amount of ammonium nitrate was obtained. Ammonia was slowly injected into the filtrate to precipitate a colored material. The injection of ammonia was stopped when 0.050 g of ammonia was added to the solution, and the colored precipitate was filtered. Ammonia was injected into the filtrate at a rate of 0.14 g/min to neutralize 2-nitrocyclododecanone. The injection of ammonia was stopped after 60 minutes, and nitrogen gas was flushed through the container to remove excess ammonia, and the ammonium salt of 2-nitrocyclododecanone was filtered.

The product was treated in accordance with the procedure of Example 1 to yield 44.0 g (0.180 mole) of the ammonium salt of 2-nitrocyclododecanone. A 34.6 g (0.443 mole) amount of DMSO was recovered by distillation under reduced pressure from the filtrate. The yield of 2-nitrocyclododecanone from the nitrooxidation reaction was 79.7%. The amount of 2-nitrocyclododecanone recovered as the ammonium salt in the separation step was 98.5%. The amount of DMSO catalyst recovered was 98.5%.

EXAMPLE 6

Nitrooxidation Condition:
  Cycloalkene — cyclododecene
  Catalyst — DMA
  Solvent — Toluene The reaction mixture of nitrooxidation was completely uniform. Ammonia was injected into the stirred reaction mixture at 0° C for 60 minutes at a rate of 0.14 g/min. The precipitated ammonium nitrate, a small amount of a colored material and the ammonium salt of 2-nitrocyclododecanone were filtered and washed with 50 cc of toluene at 0° C and 100 cc of n-hexane at 0° C. The resulting solid was transferred to a flask. A 300 cc volume of toluene was added to the solid and heated at 60° C with stirring. The heating and stirring were stopped after 20 minutes, and the mixture was cooled to room temperature and the precipitate was filtered. Most of the precipitate was ammonium nitrate. However, colored material was present in the precipitate which resulted in a colored precipitate. A 17.7 g (0.221 mole) amount of crude ammonium nitrate was obtained. Toluene was distillated from the toluene solution of 2-nitrocyclododecanone after removal of the ammonium nitrate. A 47.7 g (0.210 mole) amount of crude 2-nitrocyclododecanone was obtained. A small amount of ω-nitrododecanoic amide was present in the 2-nitrocyclododecanone obtained as an impurity and it was recrystallized in 300 cc of n-hexane. A 47.5 g (0.209 mole) amount of 2-nitrocyclododecanone was obtained. Toluene and 37.9 g (0.435 mole) of DMA were recovered by distillation under reduced pressure from the filtrate, after filtering the ammonium salt of 2-nitrocyclododecanone and ammonium nitrate.

The yield of 2-nitrocyclododecanone from the nitrooxidation reaction was 87.0%. The amount of 2-nitrocyclododecanone recovered in the separating step was 98.6%. The amount of DMA catalyst recovered was 96.9%.

EXAMPLE 7

The nitrooxidation reaction as conducted as follows: A 49.9 g amount of cyclododecene was dissolved in 600 cc of n-hexane and $NO_2$ and $O_2$ (1 : 5 mole ratio) were injected into the stirred solution at 0° C for 4 hours. By this procedure 0.50 mole of $NO_2$ was supplied and the stirring was continued for 15 minutes. To the stirred reaction mixture was added 200 g of MPD catalyst over 20 minutes and the stirring was continued for an additional 20 minutes. The reaction temperature was kept at 5° – 10° C while the reaction temperature at the addition of MPD was kept at 0° C. The nitrooxidation reaction mixture completed by this procedure was transferred to a separatory funnel and the lower phase (catalyst, nitric acid, nitrated compounds) was separated. The upper phase was twice extracted with 20 g of MPD. The catalyst was added to the lower phase. Ammonia was injected into the stirred, catalyst containing phase at 0° C to neutralize the nitric acid, and then MPD was concentrated by distillation under reduced pressure.

A 229.9 g amount of MPD was recovered. A 600 cc volume of toluene was added to the concentrated solution, and the precipitated ammonium nitrate was filtered, washed, dried and weighed. A 14.0 g (0.175 mole) amount of ammonium nitrate was obtained. Ammonia was slowly injected into the filtrate to precipitate the colored material. The injection of ammonia was stopped when 0.05 g of ammonia was supplied, and the precipitated colored material was filtered. An 8.4 g amount of ammonia was injected into the filtrate over a 60 minute period to precipitate the ammonium salt of 2-nitrocyclododecanone, and then nitrogen gas was flushed through the container to remove excess ammonia, and the ammonium salt of 2-nitrocyclododecanone was filtered.

A 39.3 g amount (0.161 mole) of the ammonium salt of 2-nitrocyclododecanone was obtained by washing and drying the material as accomplished in Example 1. A 7.5 g amount (0.076 mole) of MPD catalyst and toluene were recovered by distillation under reduced pressure from the filtrate.

The yield of 2-nitrocyclododecanone from the nitrooxidation reaction was 67.8%. The amount of the ammonium salt of 2-nitrocyclododecanone recovered in the separating step was 98.1%. The amount of MPD catalyst recovered was 98.9%.

EXAMPLE 8

Nitrooxidation Condition:
  Cycloalkene — cyclododecene
  Catalyst — DMSO
  Solvent — xylene The nitrooxidation reaction mixture was three times extracted with 20 cc of water. After the extraction, the reaction mixture was dried with anhydrous sodium sulfate, and ammonia was slowly injected into the stirred reaction mixture at 0° C to precipitate a colored material. The injection of ammonia was stopped when 0.05 g of ammonia was added to the solution, and the precipitated colored material was filtered. Ammonia was injected at a rate of 0.14 g/min for 60 minutes to precipitate the ammonium salt of 2-nitrocyclododecanone. A 53.6 g amount (0.219 mole) of the ammonium salt of 2-nitrocyclododecanone was obtained by the procedure of Example 1.

The yield of 2-nitrocyclododecanone from the nitrooxidation reaction was 91.0%. The amount of 2-nitrocyclododecanone recovered as the ammonium salt in the separating step was 99.1%.

EXAMPLE 9

The nitrooxidation reaction was conducted as follows:

A 49.9 g (0.30 mole) amount of cyclododecene was dissolved in 600 cc of n-hexane, and the mixture was stirred at 0° C. $NO_2$ and $O_2$ (1 : 5 mole ratio) were injected into the solution, and the stirring was continued for 15 minutes. After 15 minutes had passed, the reaction mixture was added to 100 cc of DMF with stirring over 20 minutes, and the stirring was continued for an additional 20 minutes. The reaction temperature was kept at 5° – 10° C, while the temperature during the addition of DMF was kept at 0° C. The nitrooxidation reaction mixture once completed, was extracted 5 times with water. After the extraction, the organic phase was dried with anhydrous sodium sulfate, and ammonia was slowly injected into the solution at 20° C with stirring to precipitate a colored material. The injection of ammonia was stopped when 0.07 g of ammonia was added to the solution, and the precipitated colored material was filtered. Ammonia was injected at the rate of 0.14 g/min for 60 minutes to precipitate the ammonium salt of 2-nitrocyclododecanone. A 40.1 g amount (0.164 mole) of the ammonium salt of 2-nitrocyclododecanone was obtained in accordance with the procedure of Example 1.

The yield of 2-nitrocyclododecanone from the nitrooxidation reaction was 68.3%. The amount of the ammonium salt of 2-nitrocylododecanone recovered in the separating step was 98.6%.

EXAMPLE 10

Nitrooxidation Condition:
 Cycloalkene — cyclooctene
 Catalyst — MPD
 Solvent — toluene The nitrooxidation reaction mixture was completely uniform. Ammonia was injected into the stirred reaction mixture at 0° C to neutralize nitric acid. The injection of ammonia was stopped when nitric acid was neutralized and the color of the reaction mixture had suddenly changed. The precipitate of ammonium nitrate was filtered, washed and dried. A 17.6 g (0.220 mole) amount of ammonium nitrate was obtained. Ammonia was slowly injected into the filtrate to precipitate the colored material. The injection of ammonia was stopped after 0.06 g of ammonia had been added. The precipitated colored material was filtered. Ammonia was further injected into the filtrate at a rate of 0.14 g/min to neutralize 2-nitrocycloctanone. The injection of ammonia was stopped after 60 minutes, and then nitrogen gas was flushed through the container to remove excess ammonia, and the resulting ammonium salt of 2-nitrocylooctanone was filtered.

A 39.3 g amount (0.209 mole) of the ammonium salt of 2-nitrocyclooctanone was obtained in accordance with the procedure of Example 1. A 34.6 g amount (0.443 mole) of MPD and toluene were recovered by distillation under reduced pressure from the filtrate.

The yield of 2-nitrocyclooctanone from the nitrooxidation reaction was 87.1%. The amount of 2-nitrocyclooctanone recovered as the ammonium salt was 98.3%. The amount of MPD catalyst recovered was 97.3%.

EXAMPLE 11

Nitrooxidation Condition:
 Cycloalkene — cyclohexene
 Catalyst — DMA
 Solvent — carbon tetrachloride The nitrooxidation reaction mixture was completely uniform. Ammonia was injected into the stirred reaction mixture at 0° C to neutralize the nitric acid. The injection of ammonia was stopped when nitric acid was neutralized and the color of the reaction mixture had suddenly changed. The ammonium nitrate precipitate was filtered, washed and dried. A 17.1 g amount (0.214 mole) of ammonium nitrate was obtained. Ammonia was slowly injected into the filtrate to precipitate the colored material. The injection of ammonia was stopped after 0.05 g of ammonia had been added, and the precipitated colored material was filtered. Ammonia was further injected into the filtrate at a rate of 0.14 g/min to neutralize 2-nitrocyclohexanone. The injection of ammonia was stopped after 60 minutes and nitrogen gas was flushed through the container to remove excess ammonia, and the resulting ammonium salt of 2-nitrocyclohexanone was filtered. A 30.1 g amount (0.188 mole) of the ammonium salt of 2-nitrocyclohexanone was obtained in accordance with the procedure of Example 1. A 44.2 g amount (0.438 mole) of DEF and carbon tetrachloride was recovered by distillation under reduced pressure from the filtrate.

The yield of 2-nitrocyclohexanone from nitrooxidation recovered was 78.5%. The amount of 2-nitrocyclohexanone recovered as the ammonium salt from the separating step was 98.2%. The amount of DEF catalyst recovered was 97.3%.

Having now fully described this invention, it will be apparent to one of ordinary skill in the art that many changes and modifications can be made thereto without departing from the spirit or scope of the invention as set forth herein.

What is claimed as new and intended to be covered by letters patent is:

1. In the preparation of 2-nitrocycloalkanone, 2-nitrocycloalkenone and 2-nitrocycloalkadienone by nitrooxidizing a cycloalkene, cycloalkadiene or cycloalkatriene in the presence of nitrogen dioxide, oxygen and an organic catalyst and separating said 2-nitrocycloalkanone, 2-nitrocycloalkenone or 2-nitrocycloalkadienone from the nitrooxidation medium, the improvement which comprises:
 precipitating ammonium nitrate by contacting said reaction mixture with gaseous ammonia;
 separating said precipitated ammonium nitrate;
 precipitating a colored impurity by contacting said reaction mixture free of ammonium nitrate with gaseous ammonia;
 filtering said precipitated colored impurity;
 precipitating the ammonium salt of 2-nitrocycloalkanone, 2-nitrocycloalkenone, or 2-nitrocycloalkadienone by contacting said reaction mixture free of ammonium nitrate and colored impurity with gaseous ammonia;
 and filtering the precipitated ammonium salt of 2-nitrocycloalkanone, 2-nitrocycloalkenone or 2-nitrocycloalkadienone.

2. The method of claim 1, wherein said ammonium salt is heat decomposed to form said 2-nitrocycloalkanone, 2-nitrocycloalkenone or 2-nitrocycloalkadienone.

3. The method of claim 1, wherein said separation is effected in the absence of water.

4. The method of claim 1, wherein ammonia is contacted with said reaction mixture until the nitric acid and a small amount of colored material are neutralized and the resulting ammonium nitrate and colored material are separated by filtration and wherein ammonia is further supplied to said filtered reaction mixture to form the ammonium salt of said 2-nitrocycloalkanone, 2-nitrocycloalkenone or 2-nitrocycloalkadienone.

5. The method of claim 1, wherein ammonia is first contacted with said nitrooxidation reaction mixture which contains a nitric acid - dimethylsulfoxide complex, by-product nitro compounds and 2-nitrocycloalkanone, 2-nitrocycloalkenone or 2-nitrocycloalkadienone until nitric acid is neutralized and 2 layers form, and the dimethylsulfoxide solution containing ammonium nitrate from said neutralized nitric acid is separated as the lower layer.

6. The process of claim 1, wherein said nitrocyclo compound is a 2-nitrocyclododecanone.

7. The method of claim 1, wherein contact of said ammonia causes separation of said reaction mixture into two layers of a catalyst solution containing ammonium nitrate and the reaction mixture, and the ammonium nitrate containing catalyst layer is separated.

8. The method of claim 5, wherein any nitric acid-dimethylsulfoxide complex which has precipitated from the reaction mixture is removed prior to contacting the reaction mixture with ammonia.

9. The method of claim 1, wherein said precipitated ammonium nitrate is separated by filtration.

10. The method of claim 1, wherein said precipitated ammonium nitrate is separated by phase separation.

* * * * *